(12) United States Patent
Omarsson et al.

(10) Patent No.: US 11,253,382 B2
(45) Date of Patent: *Feb. 22, 2022

(54) PROGRESSIVE STRAP ASSEMBLY FOR USE WITH AN ORTHOPEDIC DEVICE

(71) Applicant: Ossur hf, Reykjavik (IS)

(72) Inventors: Bjorn Omarsson, Reykjavik (IS); Arni Thor Ingimundarson, Reykjavik (IS); Valgeir Petursson, Reykjavik (IS); Hildur Inga Thorsteinsdottir, Reykjavik (IS)

(73) Assignee: OSSUR HF, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 16/713,535

(22) Filed: Dec. 13, 2019

(65) Prior Publication Data
US 2020/0113722 A1 Apr. 16, 2020

Related U.S. Application Data

(63) Continuation of application No. 15/179,169, filed on Jun. 10, 2016, now Pat. No. 10,537,458, which is a
(Continued)

(51) Int. Cl.
*A61F 5/01* (2006.01)

(52) U.S. Cl.
CPC .......... *A61F 5/0106* (2013.01); *A61F 5/0123* (2013.01); *A61F 5/0125* (2013.01)

(58) Field of Classification Search
CPC .......... A43C 11/00–1493; A43C 11/16; A43C 11/165; A43C 11/20; A43C 11/22;
(Continued)

(56) References Cited

U.S. PATENT DOCUMENTS

| 667,768 A | 2/1901 | Puy |
| 777,585 A | 12/1904 | Beatty |

(Continued)

FOREIGN PATENT DOCUMENTS

| CN | 101128169 A | 2/2008 |
| DE | 846 895 C | 8/1952 |

(Continued)

OTHER PUBLICATIONS

"Velstick semi-rigid Fastener Furnished in Separate, Mating Components", Velcro Fasteners, Spaenaur, Sep. 2, 2009, 1 Page.
(Continued)

*Primary Examiner* — Michelle J Lee
(74) *Attorney, Agent, or Firm* — Workman Nydegger

(57) ABSTRACT

A progressive strap assembly includes an elongate, inelastic body having first and second ends, and an elastic body having first and second ends, the first end of the elastic body anchored to the second end of the inelastic body. The elastic body is arranged to stretch a plurality of lengths and has a maximum stretchable length. A tension limiter is connected to the first and second ends of the elastic body and is arranged to inhibit a predetermined stretchable length of the elastic body short of the maximum stretchable length.

10 Claims, 8 Drawing Sheets

Related U.S. Application Data continuation of application No. 14/148,981, filed on Jan. 7, 2014, now Pat. No. 9,364,365.

(60) Provisional application No. 61/758,894, filed on Jan. 31, 2013, provisional application No. 61/791,518, filed on Mar. 15, 2013.

(58) Field of Classification Search
CPC .... A43C 7/00; A43C 7/06; A43C 7/08; A61F 5/01–0195; A41F 1/008; A41F 9/02; A41F 9/025; A41F 1/00; A41F 9/00; B63B 32/40–47; B63B 32/00; B63B 32/20; B63B 32/35; B63B 32/50; B63B 32/77; B63B 35/00
See application file for complete search history.

(56) References Cited

U.S. PATENT DOCUMENTS

| | | |
|---|---|---|
| 937,478 A | 10/1909 | Sims |
| 1,153,334 A | 9/1915 | Oswald |
| 1,227,700 A | 5/1917 | Tucker |
| 1,328,541 A | 1/1920 | Palmer |
| 1,510,408 A | 9/1924 | Lychou |
| 1,593,631 A | 7/1926 | Harsh |
| 1,622,211 A | 3/1927 | Sheehan |
| 1,825,898 A | 10/1931 | Coulter |
| 2,032,923 A | 3/1936 | Eldridge |
| 2,179,903 A | 11/1939 | Spears |
| 2,444,028 A * | 6/1948 | Bliss ............... A44C 5/22 2/322 |
| 2,467,907 A | 4/1949 | Peckham |
| 2,573,866 A | 11/1951 | Murphy |
| 2,717,841 A | 9/1955 | Biefeld et al. |
| 2,935,065 A | 5/1960 | Homier et al. |
| 3,031,730 A | 5/1962 | Morin |
| 3,046,981 A | 7/1962 | Biggs, Jr. et al. |
| 3,089,486 A | 5/1963 | Pike |
| 3,266,113 A | 8/1966 | Flanagan, Jr. |
| 3,463,147 A | 8/1969 | Stubbs |
| 3,514,313 A | 5/1970 | Martel et al. |
| 3,520,765 A | 7/1970 | Bateman |
| 3,528,412 A | 9/1970 | McDavid |
| 3,581,741 A | 1/1971 | Rosman |
| 3,561,436 A | 2/1971 | Gaylord, Jr. |
| 3,594,863 A | 7/1971 | Erb |
| 3,594,865 A | 7/1971 | Erb |
| 3,742,557 A | 7/1973 | Francois |
| 3,752,619 A | 8/1973 | Menzin et al. |
| 3,758,657 A | 9/1973 | Menzin et al. |
| 3,789,842 A | 2/1974 | Froimson |
| 3,804,084 A | 4/1974 | Lehman |
| 3,817,244 A | 6/1974 | Taylor |
| 3,851,357 A | 12/1974 | Ribich et al. |
| 3,877,426 A | 4/1975 | Nirschl |
| 3,916,077 A | 10/1975 | Damrau |
| 3,927,881 A | 12/1975 | Lemelson et al. |
| 3,945,046 A | 3/1976 | Stromgren |
| 3,955,565 A | 5/1976 | Johnson, Jr. |
| 4,130,115 A | 12/1978 | Taylor |
| 4,193,395 A | 3/1980 | Gruber |
| 4,204,532 A | 5/1980 | Lind et al. |
| 4,240,414 A | 12/1980 | Theisler |
| 4,269,179 A | 5/1981 | Burton et al. |
| 4,269,181 A | 5/1981 | Delannoy |
| 4,275,716 A | 6/1981 | Scott, Jr. |
| 4,280,489 A | 7/1981 | Johnson, Jr. |
| 4,291,072 A | 9/1981 | Barrett et al. |
| 4,296,744 A | 10/1981 | Palumbo |
| 4,304,560 A | 12/1981 | Greenwood |
| 4,312,335 A | 1/1982 | Daniell, Jr. |
| 4,336,279 A | 6/1982 | Metzger |
| 4,372,298 A | 2/1983 | Lerman |
| 4,381,768 A | 5/1983 | Erichsen et al. |
| 4,381,769 A | 5/1983 | Prahl |
| 4,386,723 A | 6/1983 | Mule |
| 4,396,012 A | 8/1983 | Cobiski |
| 4,470,857 A | 9/1984 | Casalou |
| 4,472,461 A | 9/1984 | Johnson |
| 4,506,661 A | 3/1985 | Foster |
| 4,528,440 A | 7/1985 | Ishihara |
| 4,554,913 A | 11/1985 | Womack et al. |
| 4,556,053 A | 12/1985 | Irons |
| 4,572,170 A | 2/1986 | Cronk et al. |
| 4,617,214 A | 10/1986 | Billarant |
| 4,632,098 A | 12/1986 | Grundei et al. |
| 4,677,713 A | 7/1987 | Copp |
| 4,693,921 A | 9/1987 | Billarant et al. |
| D292,529 S | 10/1987 | Saare |
| 4,697,583 A | 10/1987 | Mason et al. |
| 4,724,831 A | 2/1988 | Huntjens |
| 4,768,500 A | 9/1988 | Mason et al. |
| 4,775,310 A | 10/1988 | Fischer |
| D298,568 S | 11/1988 | Womack et al. |
| 4,782,605 A | 11/1988 | Cahpnick |
| 4,791,916 A | 12/1988 | Paez |
| 4,794,028 A | 12/1988 | Fischer |
| 4,801,138 A | 1/1989 | Airy et al. |
| 4,802,939 A | 2/1989 | Billarant et al. |
| 4,805,606 A | 2/1989 | McDavid, III |
| 4,854,308 A | 8/1989 | Drillio |
| 4,856,501 A | 8/1989 | Castillo et al. |
| 4,856,502 A | 8/1989 | Ersfeld et al. |
| 4,872,243 A | 10/1989 | Fischer |
| 4,922,929 A | 5/1990 | DeJournett |
| 4,933,035 A | 6/1990 | Billarant et al. |
| 4,953,543 A | 9/1990 | Grim et al. |
| 4,961,544 A | 10/1990 | Bidoia |
| 4,966,133 A | 10/1990 | Kausek |
| 4,989,593 A | 2/1991 | Campagna et al. |
| 4,991,574 A | 2/1991 | Pocknell |
| 4,991,640 A | 2/1991 | Verkindt et al. |
| 5,002,045 A | 3/1991 | Spademan |
| 5,005,527 A | 4/1991 | Hatfield |
| 5,005,627 A | 4/1991 | Hatfield |
| 5,016,621 A | 5/1991 | Bender |
| 5,018,514 A | 5/1991 | Grood et al. |
| 5,020,196 A | 6/1991 | Panach et al. |
| 5,022,109 A | 6/1991 | Pekar |
| 5,063,916 A | 11/1991 | France et al. |
| 5,067,772 A | 11/1991 | Koa |
| 5,077,870 A | 1/1992 | Melbye et al. |
| 5,085,210 A | 2/1992 | Smith, III |
| 5,112,296 A | 5/1992 | Beard et al. |
| 5,152,038 A | 10/1992 | Schoch |
| 5,154,682 A | 10/1992 | Kellerman |
| 5,157,813 A | 10/1992 | Carroll |
| 5,181,331 A | 1/1993 | Berger |
| 5,227,698 A | 7/1993 | Simpson et al. |
| 5,242,379 A | 9/1993 | Harris et al. |
| 5,267,951 A | 12/1993 | Ishii |
| 5,277,697 A | 1/1994 | France et al. |
| 5,277,698 A | 1/1994 | Taylor |
| 5,288,287 A | 2/1994 | Castillo et al. |
| 5,302,169 A | 4/1994 | Taylor |
| 5,306,230 A | 4/1994 | Bodine |
| 5,314,455 A | 5/1994 | Johnson, Jr. et al. |
| 5,316,547 A | 5/1994 | Gildersleeve |
| 5,322,729 A | 6/1994 | Heeter et al. |
| 5,334,135 A | 8/1994 | Grim et al. |
| 5,344,135 A | 9/1994 | Isobe et al. |
| 5,368,549 A | 11/1994 | McVicker |
| 5,383,845 A | 1/1995 | Nebolon |
| 5,397,296 A | 3/1995 | Sydor et al. |
| 5,415,625 A | 5/1995 | Cassford |
| 5,431,623 A | 7/1995 | Rice |
| 5,437,619 A | 8/1995 | Malewicz et al. |
| 5,445,602 A | 8/1995 | Grim et al. |
| 5,449,341 A | 9/1995 | Harris |
| 5,458,565 A | 10/1995 | Tillinghast, III et al. |
| 5,468,219 A | 11/1995 | Crippen |
| 5,472,413 A | 12/1995 | Detty |
| 5,474,524 A | 12/1995 | Carey |

(56) References Cited

U.S. PATENT DOCUMENTS

| | | |
|---|---|---|
| 5,497,513 A | 3/1996 | Arabeyre et al. |
| 5,500,268 A | 3/1996 | Billarant |
| 5,512,039 A | 4/1996 | White |
| 5,513,658 A | 5/1996 | Goseki |
| 5,514,081 A | 5/1996 | Mann |
| 5,527,269 A | 6/1996 | Reithofer |
| 5,540,982 A | 7/1996 | Scholz et al. |
| 5,542,911 A | 8/1996 | Cassford et al. |
| 5,562,605 A | 10/1996 | Taylor |
| 5,599,288 A | 2/1997 | Shirley et al. |
| 5,695,452 A | 2/1997 | Grim et al. |
| 5,614,045 A | 3/1997 | Billarant |
| 5,624,389 A | 4/1997 | Zepf |
| 5,635,201 A | 6/1997 | Fabo |
| 5,638,588 A | 6/1997 | Jungkind |
| 5,654,070 A | 8/1997 | Billarant |
| 5,656,226 A | 8/1997 | McVicker |
| 5,665,449 A | 9/1997 | Billarant |
| 5,681,271 A | 10/1997 | Nelson |
| 5,685,830 A | 11/1997 | Bonutti |
| 5,713,837 A | 2/1998 | Grim et al. |
| D392,877 S | 3/1998 | Eguchi |
| 5,737,854 A | 4/1998 | Sussmann |
| 5,759,167 A | 6/1998 | Shields, Jr. et al. |
| 5,769,808 A | 6/1998 | Matthijs et al. |
| 5,774,902 A | 7/1998 | Gehse |
| 5,795,640 A | 8/1998 | Billarant |
| 5,807,294 A | 9/1998 | Cawley et al. |
| 5,823,931 A | 10/1998 | Gilmour |
| 5,823,981 A | 10/1998 | Grim et al. |
| 5,840,398 A | 11/1998 | Billarant |
| 5,857,988 A | 1/1999 | Shirley |
| 5,857,989 A | 1/1999 | Smith, III |
| 5,865,776 A | 2/1999 | Springs |
| 5,865,777 A | 2/1999 | Detty |
| 5,865,782 A | 2/1999 | Fareed |
| 5,873,848 A | 2/1999 | Fulkerson |
| 5,891,061 A | 4/1999 | Kaiser |
| 5,891,071 A | 4/1999 | Stearns et al. |
| 5,900,303 A | 5/1999 | Billarant |
| 5,916,187 A | 6/1999 | Brill |
| 5,948,707 A | 9/1999 | Crawley et al. |
| 5,971,946 A | 10/1999 | Quinn |
| 6,010,474 A | 1/2000 | Wycoki |
| 6,021,780 A | 2/2000 | Darby |
| 6,022,617 A | 2/2000 | Calkins |
| 6,024,712 A | 2/2000 | Iglesias et al. |
| 6,063,048 A | 5/2000 | Bodenschatz et al. |
| 6,110,138 A | 8/2000 | Shirley |
| 6,111,138 A | 8/2000 | Van Wijck et al. |
| 6,142,965 A | 11/2000 | Mathewson |
| 6,152,893 A | 11/2000 | Pigg et al. |
| 6,159,583 A | 12/2000 | Calkins |
| 6,250,651 B1 | 6/2001 | Reuss et al. |
| 6,254,554 B1 | 7/2001 | Turtzo |
| 6,267,741 B1 | 7/2001 | Lerman |
| RE37,338 E | 8/2001 | McVicker |
| 6,287,268 B1 | 9/2001 | Gilmour |
| 6,289,558 B1 | 9/2001 | Hammerslag |
| 6,360,404 B1 | 3/2002 | Mudge et al. |
| 6,368,295 B1 | 4/2002 | Lerman |
| 6,402,713 B1 | 6/2002 | Doyle |
| 6,405,731 B1 | 6/2002 | Ching |
| 6,413,232 B1 | 7/2002 | Townsend et al. |
| 6,416,074 B1 | 7/2002 | Maravetz et al. |
| 6,461,318 B2 | 10/2002 | Freeman et al. |
| 6,485,776 B2 | 11/2002 | Janusson et al. |
| 6,520,926 B2 | 2/2003 | Hall |
| 6,540,703 B1 | 4/2003 | Lerman |
| 6,540,709 B1 | 4/2003 | Smits |
| D477,409 S | 7/2003 | Mills et al. |
| 6,592,538 B1 | 7/2003 | Hotchkiss et al. |
| 6,592,539 B1 | 7/2003 | Einarsson et al. |
| 6,596,371 B1 | 7/2003 | Billarant et al. |
| 6,598,250 B1 | 7/2003 | Pekar |
| 6,543,158 B2 | 8/2003 | Dieckhaus |
| 6,656,142 B1 | 12/2003 | Lee |
| 6,666,894 B2 | 12/2003 | Perkins et al. |
| 6,689,080 B2 | 2/2004 | Castillo |
| 6,726,641 B2 | 4/2004 | Chiang et al. |
| 6,735,819 B2 | 5/2004 | Iverson et al. |
| 6,740,054 B2 | 5/2004 | Stearns |
| 6,769,155 B2 | 8/2004 | Hess et al. |
| 6,773,411 B1 | 8/2004 | Alvarez |
| 6,861,371 B2 | 3/2005 | Kamikawa et al. |
| 6,861,379 B1 | 3/2005 | Blaszcykiewicz |
| 6,898,804 B2 | 5/2005 | Sandler |
| 6,898,826 B2 | 5/2005 | Draper et al. |
| 6,936,020 B2 | 8/2005 | Davis |
| D519,637 S | 4/2006 | Nordt et al. |
| D519,638 S | 4/2006 | Nordt et al. |
| 7,025,738 B2 | 4/2006 | Hall |
| D520,141 S | 5/2006 | Nordt et al. |
| D521,644 S | 5/2006 | Nordt et al. |
| 7,037,287 B2 | 5/2006 | Cormier et al. |
| 7,150,721 B2 | 12/2006 | Houser |
| 7,161,056 B2 | 1/2007 | Gudnason et al. |
| 7,169,720 B2 | 1/2007 | Etchells et al. |
| 7,198,610 B2 | 4/2007 | Ingimundarson et al. |
| 7,201,728 B2 | 4/2007 | Sterling |
| 7,303,539 B2 | 12/2007 | Binder et al. |
| 7,367,958 B2 | 5/2008 | McBean et al. |
| 7,448,115 B2 | 11/2008 | Howell et al. |
| 7,597,675 B2 | 10/2009 | Ingimundarson et al. |
| 7,648,404 B1 * | 1/2010 | Martin .................. B63B 32/45 441/70 |
| 7,698,909 B2 | 4/2010 | Hannula et al. |
| 7,713,225 B2 | 5/2010 | Ingimundarson et al. |
| 7,749,183 B2 | 7/2010 | Ingimundarson et al. |
| 7,762,973 B2 | 7/2010 | Einarsson et al. |
| 7,794,418 B2 | 9/2010 | Ingimundarson et al. |
| 7,806,842 B2 | 10/2010 | Stevenson et al. |
| 7,874,996 B2 | 1/2011 | Weinstein et al. |
| 7,905,851 B1 | 3/2011 | Bledsoe |
| 7,937,973 B2 | 5/2011 | Sorensen et al. |
| 8,016,781 B2 | 9/2011 | Ingimundarson et al. |
| 8,043,244 B2 | 10/2011 | Einarsson et al. |
| 8,216,170 B2 | 7/2012 | Ingimundarson et al. |
| 8,241,234 B2 | 8/2012 | Ingimundarson et al. |
| 8,257,293 B2 | 9/2012 | Ingimundarson et al. |
| 8,267,879 B2 | 9/2012 | Ingimundarson et al. |
| 8,277,401 B2 | 10/2012 | Hammerslag et al. |
| 8,328,746 B2 | 12/2012 | Ingimundarson et al. |
| 8,328,747 B2 | 12/2012 | Matsunaga |
| 8,425,441 B2 | 4/2013 | Ingimundarson |
| 8,556,783 B1 | 10/2013 | Ihli et al. |
| 8,585,623 B2 | 11/2013 | Ingimundarson |
| 8,864,692 B2 | 10/2014 | Ingimundarson et al. |
| 9,220,622 B2 | 12/2015 | Ingimundarson et al. |
| 9,265,644 B2 | 2/2016 | Einarsson et al. |
| 9,265,645 B2 | 2/2016 | Ingimundarson et al. |
| 9,358,146 B2 | 6/2016 | Thorsteinsdottir et al. |
| 9,364,365 B2 | 6/2016 | Omarsson et al. |
| 9,375,341 B2 | 6/2016 | Ingimundarson et al. |
| 9,474,334 B2 | 10/2016 | Jonsson et al. |
| 9,498,025 B2 | 11/2016 | Omarsson et al. |
| 9,814,615 B2 | 11/2017 | Ingimundarson |
| 10,537,458 B2 * | 1/2020 | Omarsson ............. A61F 5/0106 |
| 2001/0020143 A1 | 9/2001 | Stark et al. |
| 2001/0056251 A1 | 12/2001 | Peters |
| 2002/0032397 A1 | 3/2002 | Coligado |
| 2002/0077574 A1 | 6/2002 | Gildersleeve et al. |
| 2002/0082542 A1 | 6/2002 | Hall |
| 2002/0095750 A1 | 7/2002 | Hammerslag |
| 2002/0107464 A1 | 8/2002 | Castillo |
| 2002/0132086 A1 | 9/2002 | Su-Tuan |
| 2003/0032907 A1 | 2/2003 | Prahl |
| 2003/0069531 A1 | 4/2003 | Hall |
| 2003/0204156 A1 | 10/2003 | Nelson et al. |
| 2004/0002674 A1 | 1/2004 | Sterling |
| 2004/0054311 A1 | 2/2004 | Sterling |
| 2004/0058102 A1 | 3/2004 | Baychar |
| 2004/0137178 A1 | 7/2004 | Janusson et al. |
| 2004/0137192 A1 | 7/2004 | McVicker |

(56) References Cited

U.S. PATENT DOCUMENTS

| | | |
|---|---|---|
| 2004/0153016 A1 | 8/2004 | Salmon et al. |
| 2004/0176715 A1 | 9/2004 | Nelson |
| 2004/0199095 A1 | 10/2004 | Frangi |
| 2004/0225245 A1 | 11/2004 | Nelson |
| 2004/0267179 A1 | 12/2004 | Lerman |
| 2005/0020951 A1 | 1/2005 | Gaylord et al. |
| 2005/0038367 A1 | 2/2005 | McCormick et al. |
| 2005/0081339 A1 | 4/2005 | Sakabayashi |
| 2005/0087115 A1* | 4/2005 | Martin .............. B63B 32/45 114/39.19 |
| 2005/0159691 A1 | 7/2005 | Turrini et al. |
| 2005/0160627 A1 | 7/2005 | Dalgaard et al. |
| 2005/0273025 A1 | 12/2005 | Houser |
| 2005/0279797 A1* | 12/2005 | Martin .............. B63H 8/56 224/637 |
| 2006/0015980 A1 | 1/2006 | Nordt, III et al. |
| 2006/0020237 A1 | 1/2006 | Nordt, III et al. |
| 2006/0026732 A1 | 2/2006 | Nordt, III et al. |
| 2006/0026733 A1 | 2/2006 | Nordt, III et al. |
| 2006/0026736 A1 | 2/2006 | Nordt, III et al. |
| 2006/0030802 A1 | 2/2006 | Nordt, III et al. |
| 2006/0030803 A1 | 2/2006 | Nordt, III et al. |
| 2006/0030804 A1 | 2/2006 | Nordt, III et al. |
| 2006/0030805 A1 | 2/2006 | Nordt, III et al. |
| 2006/0030806 A1 | 2/2006 | Nordt, III et al. |
| 2006/0070164 A1 | 4/2006 | Nordt, III et al. |
| 2006/0070165 A1 | 4/2006 | Nordt, III et al. |
| 2006/0084899 A1 | 4/2006 | Verkade et al. |
| 2006/0090806 A1 | 5/2006 | Friedline et al. |
| 2006/0094999 A1 | 5/2006 | Cropper |
| 2006/0116619 A1 | 6/2006 | Weinstein et al. |
| 2006/0135900 A1 | 6/2006 | Ingimundarson et al. |
| 2006/0135902 A1 | 6/2006 | Ingimundarson et al. |
| 2006/0135903 A1 | 6/2006 | Ingimundarson et al. |
| 2006/0155229 A1 | 7/2006 | Ceriani et al. |
| 2006/0156517 A1 | 7/2006 | Hammerslag et al. |
| 2006/0191110 A1 | 8/2006 | Howell et al. |
| 2007/0083136 A1 | 4/2007 | Einarsson |
| 2007/0106191 A1 | 5/2007 | Mueller et al. |
| 2007/0130665 A1 | 6/2007 | Wang |
| 2007/0167892 A1 | 7/2007 | Gramza et al. |
| 2007/0167895 A1 | 7/2007 | Gramaza et al. |
| 2007/0185425 A1 | 8/2007 | Einarsson et al. |
| 2007/0225824 A1 | 9/2007 | Einarsson |
| 2008/0034459 A1 | 2/2008 | Nordt, III et al. |
| 2008/0066272 A1* | 3/2008 | Hammerslag .......... A43C 11/14 24/712 |
| 2008/0195014 A1 | 8/2008 | Ingimundarson et al. |
| 2008/0229556 A1 | 9/2008 | Hammer |
| 2008/0294079 A1 | 11/2008 | Sterling et al. |
| 2009/0099562 A1 | 4/2009 | Ingimudarson et al. |
| 2009/0126413 A1 | 5/2009 | Sorensen et al. |
| 2009/0259154 A1 | 10/2009 | Nace |
| 2010/0068464 A1 | 3/2010 | Meyer |
| 2010/0125231 A1 | 5/2010 | Knecht |
| 2011/0057466 A1 | 3/2011 | Sachee et al. |
| 2011/0275970 A1 | 11/2011 | Paulos et al. |
| 2012/0010547 A1 | 1/2012 | Hinds |
| 2012/0046585 A1 | 2/2012 | Lee et al. |
| 2012/0090624 A1 | 4/2012 | Chang |
| 2012/0109031 A1 | 5/2012 | Vollbrecht et al. |
| 2012/0220910 A1 | 8/2012 | Gaylord et al. |
| 2013/0184628 A1 | 7/2013 | Ingimundarson et al. |
| 2013/0245523 A1 | 9/2013 | Romo |
| 2014/0121579 A1 | 5/2014 | Hinds |
| 2014/0194801 A1 | 7/2014 | Ingimundarson et al. |
| 2014/0214016 A1 | 7/2014 | Ingimundarson et al. |
| 2014/0257158 A1 | 9/2014 | Lee et al. |
| 2015/0032041 A1 | 1/2015 | Ingimundarson et al. |
| 2015/0290014 A1 | 10/2015 | Anglada et al. |
| 2016/0193066 A1 | 7/2016 | Albertsson et al. |
| 2016/0242945 A1 | 8/2016 | Thorsetinsdottir et al. |
| 2016/0278959 A1 | 9/2016 | Omarsson et al. |
| 2016/0296360 A1 | 10/2016 | Ingimundarson et al. |
| 2017/0065037 A1 | 3/2017 | Omarsson et al. |
| 2017/0348130 A1 | 12/2017 | Petursson |
| 2017/0348131 A1 | 12/2017 | Petursson |

FOREIGN PATENT DOCUMENTS

| | | |
|---|---|---|
| DE | 100 04 561 A1 | 8/2001 |
| DE | 20 2004 012 892 U1 | 10/2004 |
| EP | 0 050 769 A1 | 5/1985 |
| EP | 0 196 204 A2 | 10/1986 |
| EP | 0 611 069 A | 8/1994 |
| EP | 1016351 A1 | 7/2000 |
| EP | 2612624 A1 | 7/2013 |
| EP | 2612626 A2 | 7/2013 |
| FR | 2 399 811 A1 | 3/1979 |
| FR | 2 553 996 A1 | 5/1985 |
| FR | 2 766 359 A1 | 1/1999 |
| GB | 1209413 A | 10/1970 |
| GB | 2 136 294 A | 9/1984 |
| GB | 2 455 972 A | 7/2009 |
| WO | 88/01855 A1 | 3/1988 |
| WO | 94/00082 A1 | 1/1994 |
| WO | 00/49982 A1 | 8/2000 |
| WO | 00/70984 A1 | 11/2000 |
| WO | 2006/015599 A1 | 2/2006 |
| WO | 2006/069221 A2 | 6/2006 |
| WO | 2006/069222 A2 | 6/2006 |
| WO | 2008/115376 A1 | 9/2008 |
| WO | 2009052031 A1 | 4/2009 |
| WO | 2010/117749 A2 | 10/2010 |
| WO | 2011/073803 A2 | 6/2011 |

OTHER PUBLICATIONS

Article: "An Orthosis for Medial or Lateral Stabilization of Arthritic Knees", by S. Cousins and James Foort, Orthotics and Prosthetics, vol. 29, No. 4, pp. 21-26, Dec. 1975.
Advertising Brochure: "NUKO Camp", 6 pages, Camp International, Inc. Jackson, MI (1984).
Advertising Brochure: "Lerman Multi-Ligaments Knee Control Orthosis", 2 pages, Zinco Industries, Inc. of Montrose, CA (1985).
"Information on Flexible Polyurethane Foam", In Touch, vol. 4, No. 3, Jul. 1994, 5 pages.
Advertisement: "Custom Engineered Fabrics and Products for Advanced High Performance", 1 page, Gehring Textiles (visited Dec. 15, 2005), http://www.gehringtextiles.com/d3.html.
Article: "Osteoarthritis of the Knee: An Information Booklet", Arthritis Research Campaign (visited Dec. 14, 2004) http://www.arc.org.uk/about_arth/booklets/6027/6027.htm.
Advertising Brochure: "Freedom to Perform-Fusion", 5 pages, (2005).
Advertising Brochure: "Fusion", 6 pages, Breg, Inc. of Vista, CA (2005).
Advertising Brochure: "Fusion XT", 2 pages, Breg, Inc. of Vista, CA (2005).
Advertising Brochure: "Anderson Knee Stabler", 4 pages, Omni Scientific, Inc. of Lafayette, CA. Feb. 7, 2013.
Advertising Brochure: "OTI Brace", 4 pages, Orthopedic Technology, Inc. of San Leandro, CA. Feb. 7, 2013.
Advertising Brochure: "The Four Axioms of Functional Bracing", 2 pages, Bledsoe by Medical Technology, Inc. (2005).
Advertising Brochure: "The Leader in Knee Motion Management," 8 pages. Donjoy, Carsbad, CA. Feb. 7, 2013.
Advertising Brochure: "The Lenox Hill Lightweight", 1page, Lenox Hill Brace, Inc., New York, NY. Feb. 7, 2013.
Advertising Brochure: "XCL System", 2 pages, Innovation Sports of Foothill Ranch, CA. Feb. 7, 2013.
Advertising Brochure: "The 9 Innovations of the Axiom Custom Brace", 1 page, Bledsoe, Medical Technology, Inc. (2005).
Technical Manual: Bellacure: Restore Your Lifestyle, 10 pages, Bellacure, Inc. (2005).
Technical Manual: "Boa Technology", 3 pages, Boa Technology, Inc. of Steamboat Springs, CO, Feb. 7, 2013.

(56) References Cited

OTHER PUBLICATIONS

Advertising Brochure: "GII Unloader Select", 2 pagse, Ossur HF of Reykjavik, Iceland (visited Mar. 8, 2005), http://www.ossur.com/pring.asp?pageID=1729.

Advertisement: "McDavid Knee Guard and 155 Ligament Augmentation System", 3 pages, Advanced Brace of Irving TX (visited Mar. 8, 2005), http://www.supports4u.com/mcdavid/kneeguard.htm.

Advertisement: "Triax", 1 page, Lanxess AG (visited Mar. 8, 2005), http://www.techcenter.lanxess.com/sty/emea/en/products/description/57/index/jsp?print=true&pid=57.

Reference: "Anatomical Planes", 1 page, (visited Mar. 26, 2005), http://www.spineuniverse.com/displayarticle.phpo/article1023.html.

Advertisement: "M2 Inc. Parts Catalog", 3 pages, M2 Inc. of Winooski, VT (visited Mar. 29, 2005), http://www.m2intl.com/medical.MedClsr.htm.

Advertisement: "Axiom", 3 pages, Bledsoe by Medical Technology, Inc. (visited Jun. 15, 2005), http://www.bledsoebrace.com/custom/axiom.asp.

Advertisement: "Bellacure: The Treatment Device", 6 pages, Bellacure, Inc. (visited Jan. 5, 2006), http://www.bellacure.com/products/index/html.

Advertisement: "Lerman 3-Point Knee Orthosis", 2 pages, Becker Orthopedic of Troy, MI (visited Feb. 26, 2006), http://www.beckerortho.com/knee/3-point/htm.

Article: "Thermoplastic Elastomers TPE, TPR, TPV", 6 pages (visited Mar. 14, 2007), http://www.bpf.co.uk.bpfindustry/plastics_thermplasrubber_TBR.cfm.

\* cited by examiner

PROGRESSIVE STRAP ASSEMBLY FOR USE WITH AN ORTHOPEDIC DEVICE

CROSS-REFERENCE TO RELATED APPLICATIONS

This application is a continuation of U.S. application Ser. No. 15/179,169 filed Jun. 10, 2016 which is a continuation of Ser. No. 14/148,981, filed Jan. 7, 2014, now U.S. Pat. No. 9,364,365, which claims the benefit of U.S. provisional application No. 61/758,894, filed on Jan. 31, 2013, and U.S. provisional application No. 61/791,518, filed on Mar. 15, 2013, both of which are incorporated herein by their entirety.

FIELD OF THE DISCLOSURE

The embodiments of this disclosure are directed to a strap, particularly to a progressive strap assembly for use with an orthopedic device.

BACKGROUND

Knee braces and supports are widely used to treat a variety of knee infirmities. Such braces may be configured to impart forces or leverage on the limbs surrounding the knee joint to relieve compressive forces within a portion of the knee joint or to reduce the load on that portion of the knee. If knee ligaments are weak and infirm, a knee brace may stabilize, protect, support, or rehabilitate the knee.

The knee is acknowledged as one of the weakest joints in the body and serves as the articulating joint between the thigh and calf muscle groups. The knee is held together primarily by small but powerful ligaments. Knee instability arising out of cartilage damage, ligament strain, and other causes is relatively commonplace since the knee joint is subjected to significant loads during the course of almost any kind of physical activity that requires using the legs.

A healthy knee has an even distribution of pressure in both the medial and lateral compartments of the knee. It is normal for a person with a healthy knee to place a varus moment on the knee when standing so the pressure between the medial and lateral compartments is uneven but still natural.

One type of knee infirmity that many individuals are prone to having is compartmental osteoarthritis. Compartmental osteoarthritis may arise when there is a persistent uneven distribution of pressure in one of the medial and lateral compartments of the knee. Compartmental osteoarthritis can be caused by injury, obesity, misalignment of the knee, or aging of the knee.

A major problem resulting from osteoarthritis of the knee is that the smooth cartilage lining the inside of the knee wears away. This leads to a narrowing of the joint space, and therefore the knee develops cysts and erosions in the bone ends. Because of the narrowing of the joint, bone comes directly in contact with bone, and an uneven distribution of pressure develops across the knee, which may cause the formation of bone spurs around the joint. All of these changes ultimately lead to increasing pain and stiffness of the joint.

While there are no cures to osteoarthritis, there are many treatments. Individuals who have a diagnosis of isolated medial compartmental osteoarthritis of the knee are confronted with a variety of treatment options such as medications, surgery, and nonsurgical interventions. Nonsurgical interventions include using canes, lateral shoe wedges, and knee braces.

Knee bracing is useful to provide compartment pain relief by reducing the load on the compartment through applying an opposing external valgus or varus moment about the knee joint. Unloading knee braces have been shown to significantly reduce osteoarthritis knee pain while improving knee function.

Straps used in an unloading knee brace are commonly referred to as dynamic force straps (DFS), and create unloading as the straps become taut, yet due to the mechanics of the brace, the straps only become taut when the knee is close to full extension. As shown in FIG. 1, the unloading is only achieved at low degrees of flexion. In referring to FIG. 2, during normal gait, loading of the knee only happens when flexion angles are less than 15-20 degrees.

During activities, such as walking up stairs and steep slopes, loading can occur at greater flexion angles than those required under normal walking circumstances. The knee angles during stair ascent can be seen in FIG. 3, which demonstrates that unloading should be provided for flexion at greater angles. Conventional dynamic force straps fall short of providing unloading at such greater angles.

Microfracture surgery can be an indication for unloading braces. Microfracture surgery is only indicated if the unloading type brace can provide unloading at the flexion at which the cartilage defect is part of the joint contact surface. Such unloading at the required degree of flexion is not typically obtainable with conventional dynamic force straps.

SUMMARY

Embodiments of the disclosure are related to a progressive force strap assembly for use with an orthopedic device. By "progressive," the disclosure connotes that the strap assembly is capable of providing a consistent or maintaining a minimum level of force on a user when the strap assembly is tensioned over the course of a specified movement. In an unloading knee brace, the strap assembly maintains a minimum force applied to a joint over the entire gait cycle.

In an embodiment of the disclosure, a progressive force strap includes an elongate, inelastic body having first and second ends, and an elastic body having first and second ends. The first end of the elastic body is secured to the second end of the inelastic body, is arranged to stretch a plurality of lengths, and has a maximum stretchable length. A tension limiter is connected to the first and second ends of the elastic body and is arranged to inhibit a predetermined stretchable length of the elastic body short of the maximum stretchable length.

While the inelastic body and the tension limiter are preferably flexible, the elastic body is both flexible and elastic, whereby being elastic it can stretch and return to a predetermined shape with no permanent or only minimal deformation. The inelasticity of the inelastic body prohibits stretching beyond its predefined length, width, or other dimension.

A dosing device may be coupled to the second end of the elastic body and permit incremental adjustment of the inelastic body relative thereto. The dosing device may include a tensioning mechanism and an elongate element adjustably secured to a retainer and coupled to the tensioning mechanism. The elongate element may be within a sleeve-forming part of the dosing device. The sleeve may define a plurality of indicia representing loading levels. Other types of dosing devices may be used including those having a linear ratchet.

In a variation of the progressive force strap assembly, the tension limiter includes a plurality of stitches in a predetermined pattern and limits elongation of the elastic body. The plurality of stitches may be arranged in a non-linear configuration when the elastic body is in a non-tensioned state. The stitches are adapted to stretch and elongate when the elastic body is in a tensioned state and inhibit stretching of the elastic body before it reaches its maximum stretchable limit. Alternatively, the stitches may be arranged in a linear configuration so that they are stretchable but reach their own maximum stretchable limit before the elastic body reaches its maximum stretchable limit.

In yet another variation of the progressive force strap assembly, the tension limiter is an inelastic segment separate from the inelastic body and has first and second ends secured to the first and second ends of the elastic body. The inelastic segment has a length greater than the elastic body when the elastic body is in a relaxed condition, but the length is less than the maximum stretchable length of the elastic body. The tension limiter may have a width less than the width of the elastic body and may be more flexible and/or lightweight than the elastic and inelastic bodies.

A dosing device may be connected to the second end of the elastic body and a second end of the tension limiter. A sleeve may be connected to the dosing device through which the second ends of the elastic body and the tension limiter are arranged to slide upon operation of the dosing device. The dosing device may include a track and the second ends of the elastic body and the tension limiter may secure to a retainer slidably engaging the track arranged to guide movement of the retainer.

In another embodiment, the first end of the elastic body may be anchored to the inelastic body and have a length short of a total length of the inelastic body. The elastic body may overlap at least a segment of the total length of the inelastic body. The length of the elastic body may span a segment of the inelastic body short of the total length. The elastic body may be anchored at first and second locations within the total length of the inelastic body.

In a non-tensioned state, the elastic body spans a segment distance defined between first and second locations of the inelastic body. The elastic body has a shorter length in the non-tensioned state than the segment distance of the inelastic body. In a tensioned state, a stretched length of the elastic body is limited by the segment distance of the inelastic body.

The elastic body may have generally the same width as the inelastic body, but generally has a shorter length than the inelastic body. Also, at least with unloading braces, the elastic body is preferably connected at an end of the inelastic body proximate or adjacent to the orthopedic device.

Variations of the elastic and inelastic bodies may be employed in combination with or without a tension limiter, and various material properties of the elastic and inelastic bodies and tension limiter may be selected accordingly. Variations may also include modifications of placement of the elastic body relative to the inelastic body, and the embodiments are not limited to the inelastic body being at or proximate to an end portion of the progressive strap assembly.

An orthopedic device may include the progressive strap assembly under the disclosure.

The orthopedic device includes a frame having at least first and second portions, and a progressive force strap assembly including an elongate, inelastic body having first and second ends and an elastic body having first and second ends. The first end of the elastic body is anchored to the second end of the inelastic body, and the first end of the inelastic body is connected to the first portion of the frame, and the second end of the elastic body is connected to the second portion of the frame. The progressive force strap assembly is adjustable in length and tensionable between the first and second frame portions.

Various methods may regulate the stretching of the elastic strap body, including the provision of a tension limiter in combination with a dosing device. Such methods with the dosing device include regulating a variable or progressive strap tension over a limb or limbs of a user and operatively accounting for movement of the limb or limbs at a joint by adjusting tension in the progressive strap assembly. The methods include preventing stretching of the elastic body beyond a predefined length by a tension limiter, whereby such predefined length is preferably short of a predetermined maximum length of the elastic body.

While described with a knee unloading brace, the progressive force strap assembly may be employed in a variety of orthopedic devices that include straps applied a force to a body.

The numerous advantages, features, and functions of the embodiments will become readily apparent and better understood in view of the following description and accompanying drawings. The following description is not intended to limit the scope of the strap assembly, but instead merely provides exemplary embodiments for ease of understanding.

BRIEF DESCRIPTION OF THE DRAWINGS

These and other features, aspects, and advantages of the present invention will become better understood regarding the following description, appended claims, and accompanying drawings.

In the various figures, similar elements are provided with similar reference numbers. The figures are not drawn to scale or proportion, but instead are drawn to provide a better understanding of the components and are not intended to be limiting in scope but rather provide exemplary illustrations.

DETAILED DESCRIPTION OF VARIOUS EMBODIMENTS

Figure 1:
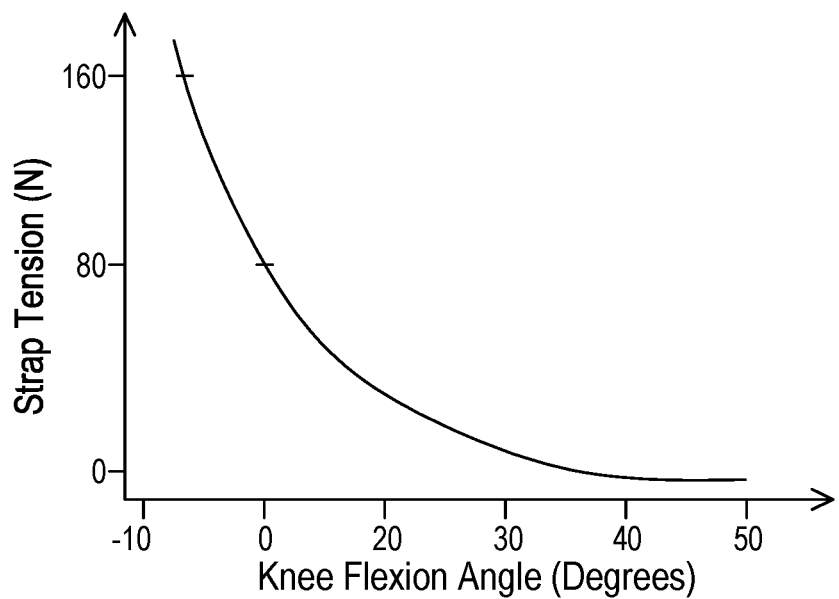
FIG. 1 is a graph showing a force curve of a prior art dynamic force strap.
Figure 2:
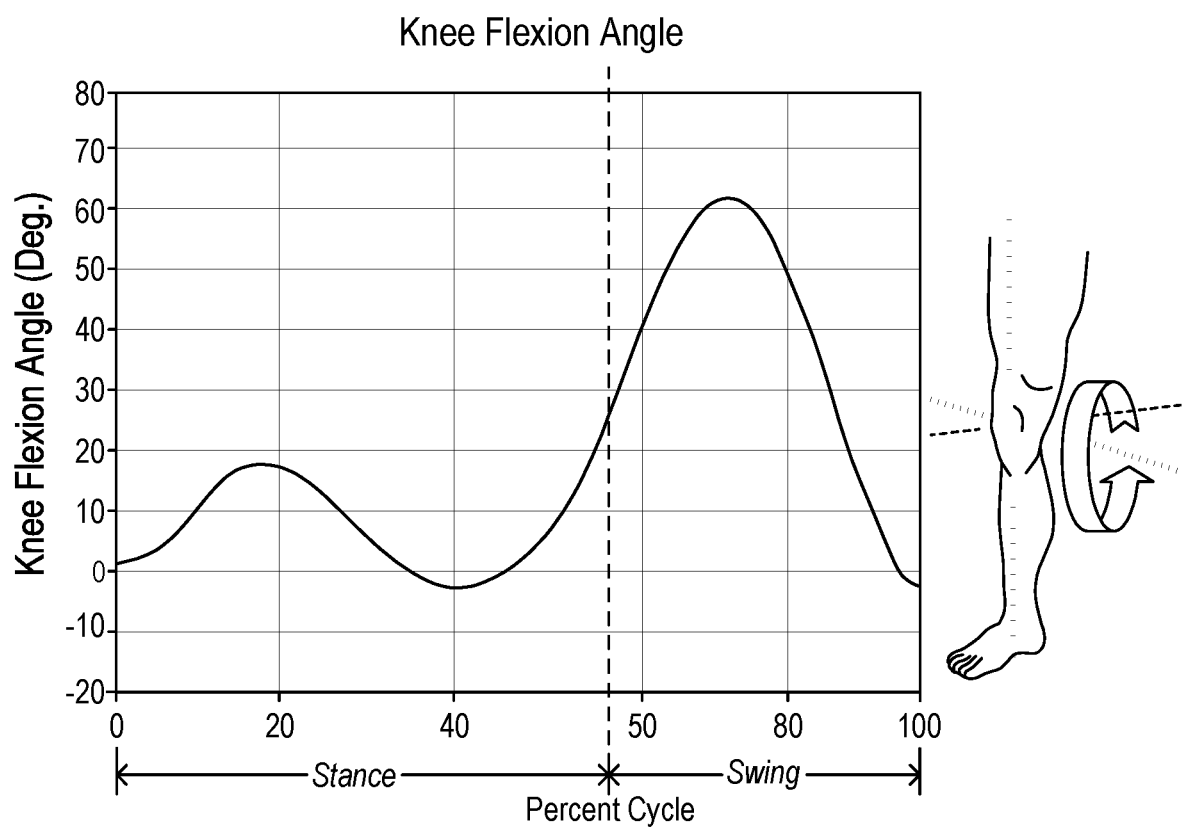
FIG. 2 is a graph showing a knee flexion angle over gait.
Figure 3:
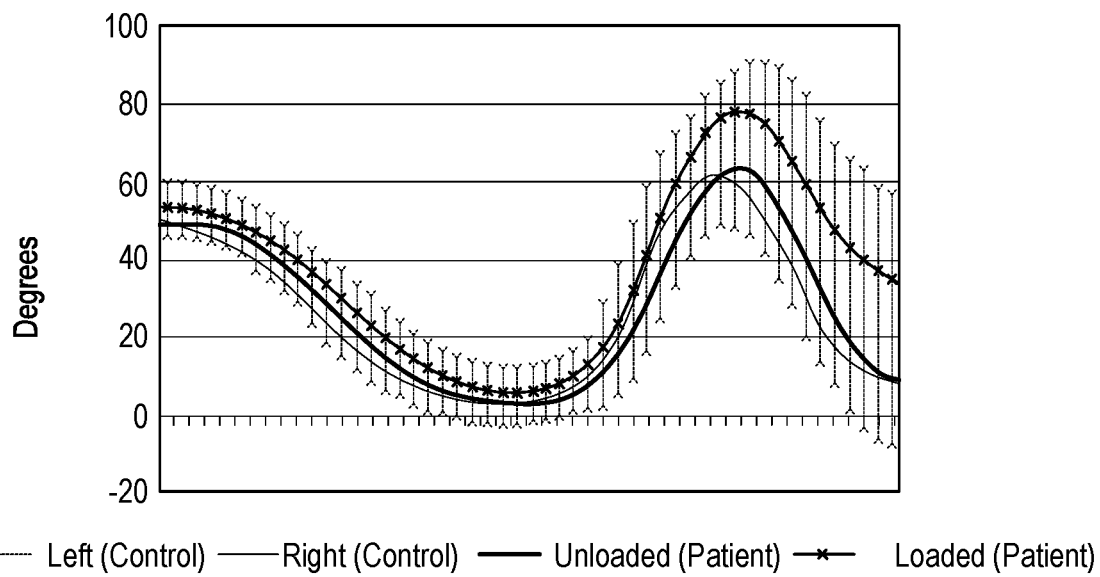
FIG. 3 is a graph showing knee flexion during stair walking.
Figure 4:
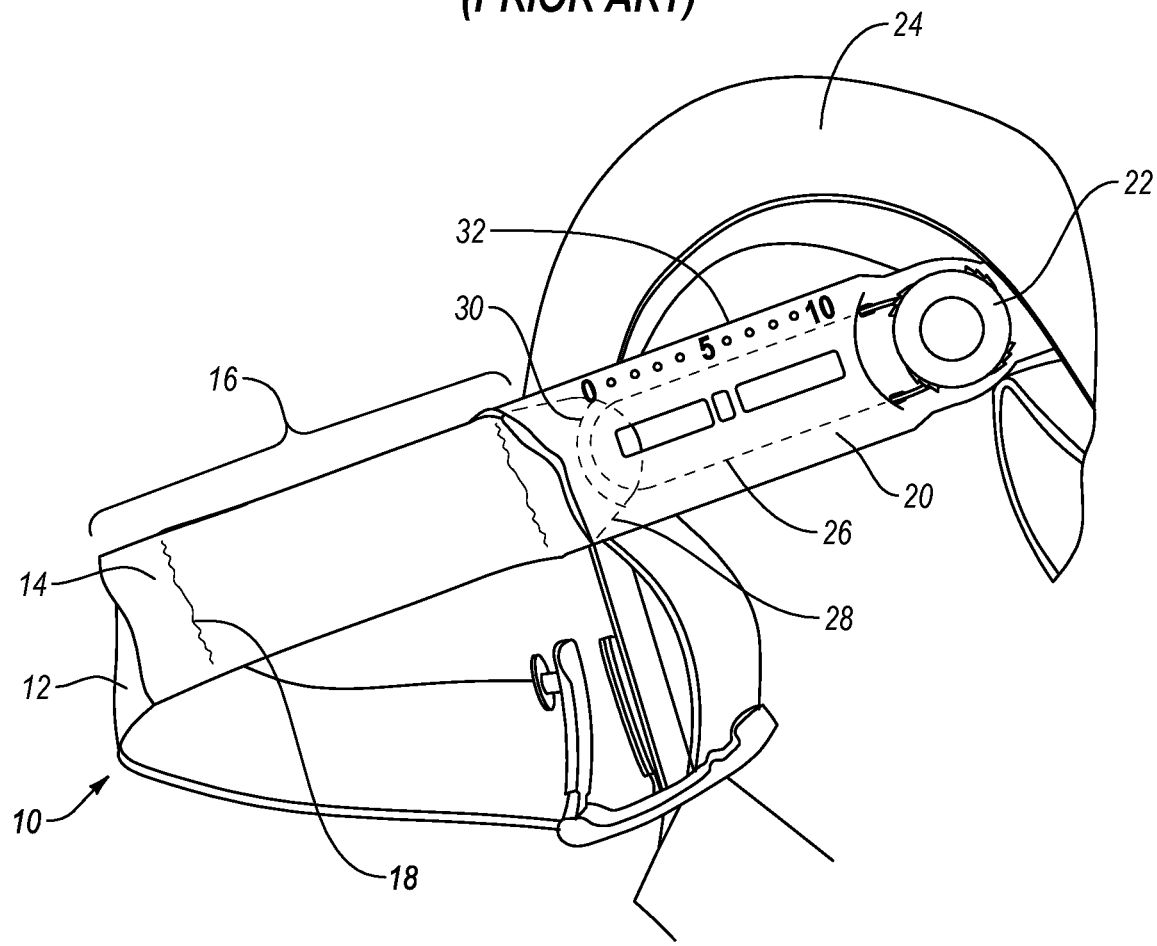
FIG. 4 is a schematic view of an embodiment of a progressive force strap according to the disclosure.

Referring to FIG. 4, a progressive strap assembly 10 includes an elongate, inelastic body 12 having first and second ends, and an elastic body 14 having first and second ends. The first end of the elastic body 14 is anchored to the second end of the inelastic body 12 along an anchor point including stitches 18. In a non-tensioned state, the elastic body 14 has a first length 16 multiplied when the elastic body 14 is in a tensioned, stretched state.

The strap assembly 10 is connected to first and second portions of an orthopedic device frame 24, such as a knee unloading brace. The strap assembly 10 is adjustable in length and progressively tensionable between the first and second frame portions of the orthopedic device. The elastic body 14 is preferably connected to an end of the inelastic body 12, and is located proximate or adjacent to the orthopedic device.

A dosing device may be coupled to the second end along an anchor point of the elastic body 14 and permits incremental adjustment of the inelastic body 12 relative thereto. The dosing device may include a tensioning mechanism 22 and an elongate element or cable 26 adjustably secured to a retainer 28 and coupled to the tensioning mechanism 22. The cable 26 may be within a sleeve 20 forming part of the dosing device. The sleeve 20 may define a plurality of indicia 32 representing loading levels.

The dosing device may be of the type described in U.S. application Ser. No. 13/739,491, published as U.S. patent application publication no. 2013/01846627, published on Jul. 18, 2013, and the linear or dial tensioning mechanisms may be of the types described in U.S. Pat. No. 7,198,610, granted on Apr. 3, 2007, both of which are incorporated herein by their entirety. Examples of the orthopedic device and the manner in which the strap assembly secures to portions of the orthopedic device are provided in U.S. application Ser. No. 13/739,491 and U.S. Pat. No. 7,198,610.

The inelastic body may be constructed from a variety of textiles and other suitable materials, and the reasons for the inelastic strap are as taught in U.S. Pat. No. 7,198,610. The elastic body may be formed by any suitable elastic material, including textiles, polymeric materials, rubber, etc.

Figure 5:
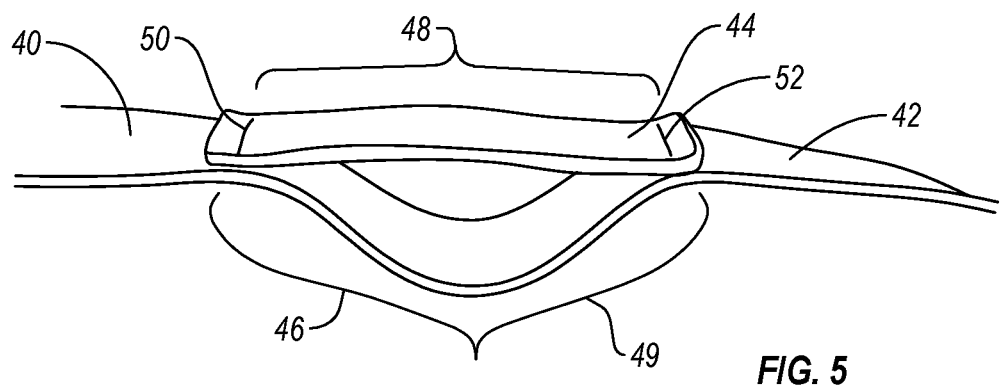
FIG. 5 is a schematic view of another embodiment of a progressive force strap in a non-tensioned state.
Figure 6:
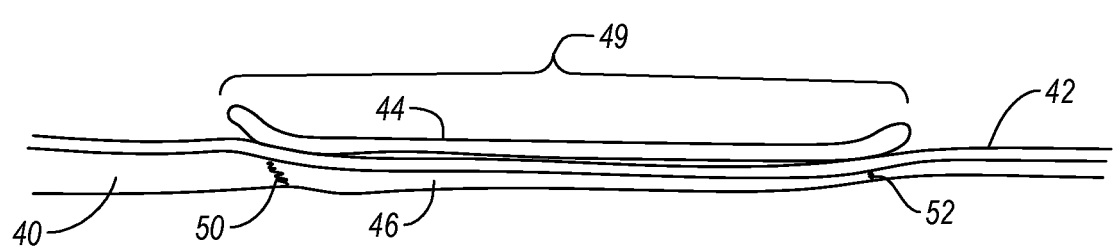
FIG. 6 is a schematic view of the dynamic force strap of FIG. 5 in a tensioned state.

Referring to the embodiment of FIGS. 5 and 6, the progressive strap assembly 40 includes an elongate, inelastic body 42 having a total length and an elastic body 44 having first and second ends. The first end of the elastic body 44 is anchored to the inelastic body 42 at first and second locations 50, 52, respectively, and has a length 48 in a non-tensioned state short of the total length of the inelastic body 42. The elastic body 44 overlaps at least a length segment 49 of the total length of the inelastic body 42. The length 48 of the elastic body 44 may span the length segment 49 of the inelastic body 42 short of the total length. The first and second locations 50, 52 are preferably within the total length of the inelastic body 42.

The non-tensioned length 48 of the elastic body 44 is preferably less than the length segment 49 of the inelastic body 42.

When the elastic body 44 is in the non-tensioned state, the elastic body 44 generally spans the length segment 49 defined between first and second locations of the inelastic body 42. The inelastic body 42 is looped or bows outwardly to form a slackened segment 46 to accommodate the difference in length among the length segment 49 of the inelastic body 42 and the non-tensioned length 48 of the elastic body 44.

When the strap assembly is in a tensioned state, the stretched length of the elastic body 44 is limited by the length segment 49 of the inelastic body 42 in which the slackened region 46 is removed and the tensioned length of the elastic body 44 and the segment length 49 are the same. The slackened region 46 is removed by the inelastic and the elastic bodies 42, 44 therefore being coextensive across the segment length 49, as depicted in FIG. 6. The inelasticity of the inelastic strap 42 in combination with the removal of the slackened region 46, and the elasticity of the elastic body 44 makes both coextensive, whereas in the non-tensioned state, the elastic and inelastic bodies are not coextensive since the elastic body 44 is shorter than the segment length 49.

Figure 7:
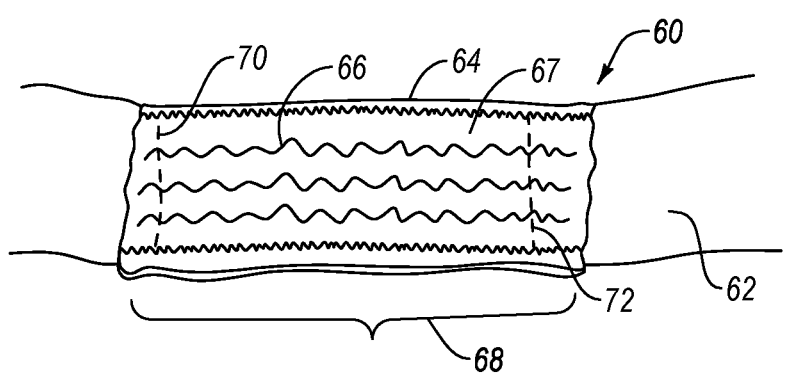
FIG. 7 is a schematic view of another embodiment of another progressive force strap in a non-tensioned state.
Figure 8:
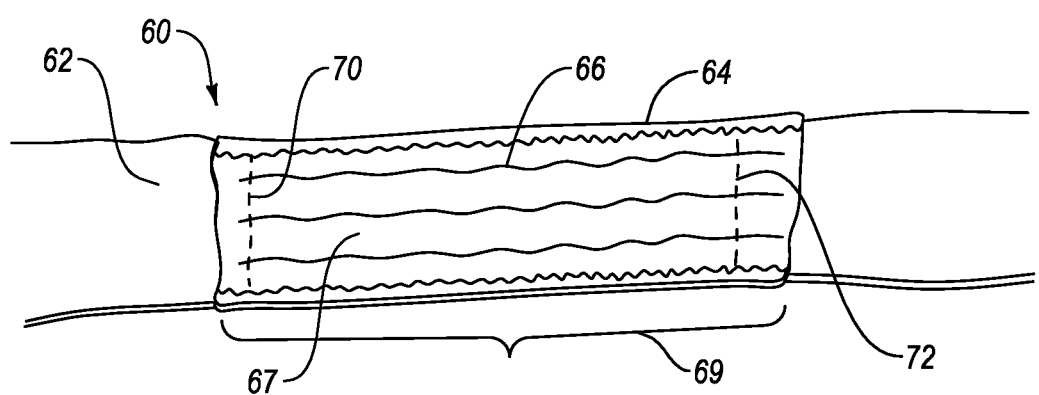
FIG. 8 is a schematic view of the dynamic force strap of FIG. 7 in a tensioned state.

Another embodiment of the strap assembly 60 is in FIGS. 7 and 8. The strap assembly 60 includes an inelastic body 62 and an elastic body 64 having a plurality of stitches 66 that are arranged in a zig-zag configuration when the elastic body 64 is in a non-tensioned state.

The embodiment relies on the misalignment of stitches or other means relative to the length of the elastic body when the elastic body is in a non-tensioned state and an alignment of the stitches or other means relative to the length of the elastic body when it is in a tensioned state.

The elastic body 64 has first and second ends 70, 72, respectively, which are anchored at first and second ends of first and second segments of the inelastic body 62. Alternatively, only the first end 70 is anchored to an end of the inelastic body 62, and the second end 72 is secured to the orthopedic device frame or other component connected to the orthopedic device frame.

The stitches 66 are preferably formed from an inelastic thread, whereas the remainder 67 of the inelastic body 62 is elastic. The elastic body 64 has a first length 68 in the non-tensioned state and a maximum second length 69 in a fully tensioned state. In the fully tensioned state, the stitches 66 are elongated from the zig-zag configuration and limit further stretching of the elastic body 64.

The stitches are not limited to a zig-zag configuration and may be arranged in other configurations that permit elongation of the elastic body but also are adapted to limit stretching of the elastic body after a certain length. The embodiment is not limited to stitches, but other means may be in combination with the remainder to allow stretching but inhibit a certain length of stretching.

Figure 9:
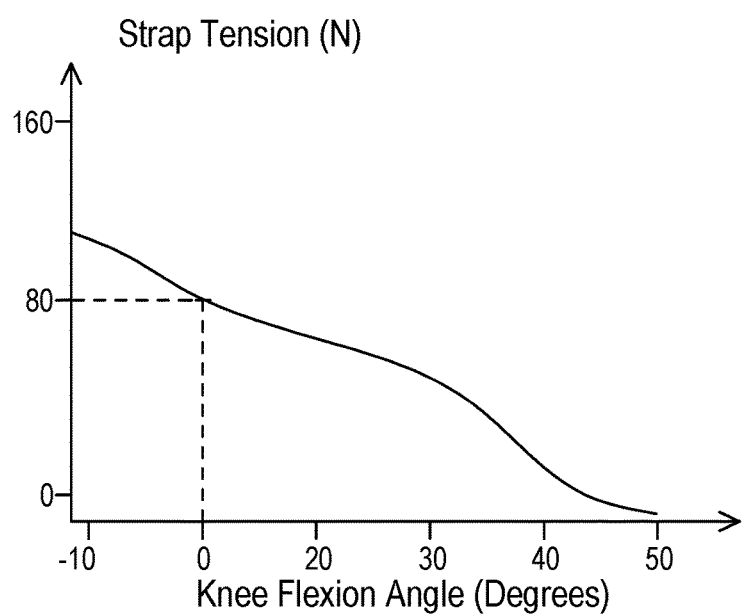
FIG. 9 is an exemplary graph showing a force curve of a progressive force strap.

FIG. 9 shows how the progressive strap assembly of the disclosure makes the force curve of a dynamic force strap more progressive over the prior art strap assemblies. The advantage of the progressivity of the strap assembly is it allows for better improvement of pain relief experienced by users of unloading type braces that use dynamic force straps. The strap assembly of the disclosure unloads through a greater range of motion and allows for better pain relief when mounting stairs. It also assists in microfracture surgery rehabilitation.

Constant tension in the strap assembly prevents migration of the orthopedic device since there is a constant force applied over movement of the user. This allows for better comfort and compliance.

Figure 10:
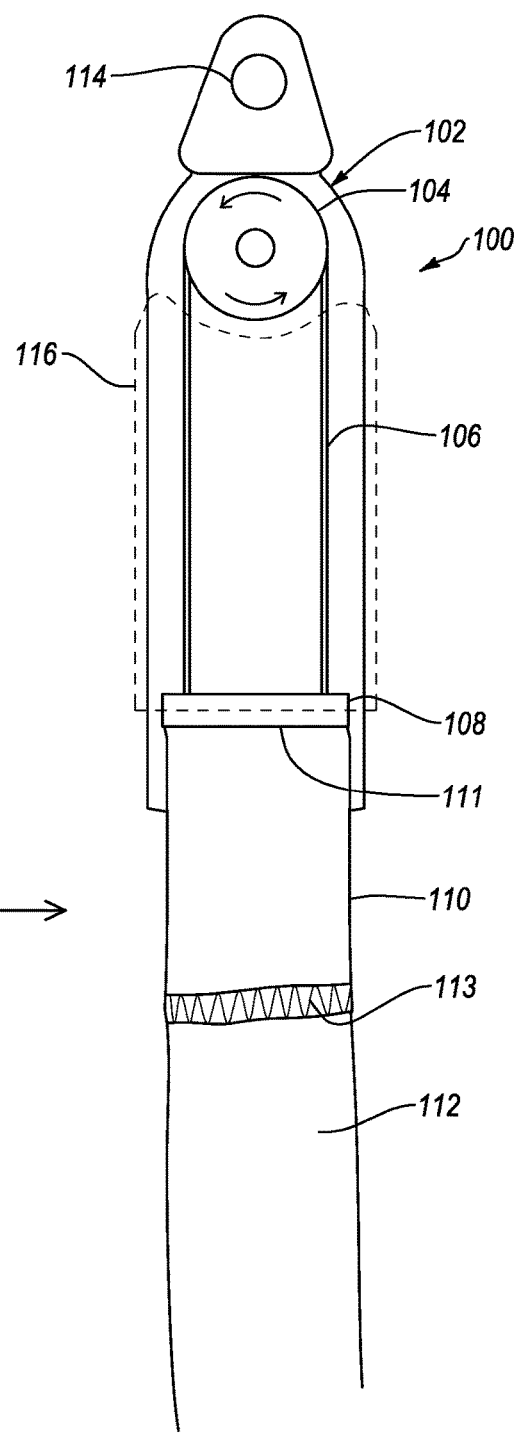
FIG. 10 is another exemplary embodiment of a progressive strap assembly including a tensioning mechanism.

FIG. 10 illustrates another progressive strap assembly 100 including a base plate 102, a tensioning mechanism 104, and elongate elements or cables 106 extending from the tensioning mechanism 104 and secured to a retainer 108 mounted on a first end 111 of an elastic body 110. The elastic body 110 has a second end secured to another strap body 112, which is preferably inelastic, along stitching 113 or other interface used to connect the elastic body 110 and the strap body 112. A first end of the base plate 102 is pivotally mounted at pivot point 114 to a shell, buckle, or other brace component. A flexible sleeve 116 is arranged to cover the cables 106 and portions of the base plate 102. The retainer 108 has first and second ends, and the second end of the retainer 108 and the first end 111 of the elastic body 110 are arranged to linearly slide within the sleeve 116.

In operation, the cables 106 transmit tension through the elastic body 110 for reasons discussed above. The inelastic body 112 forms the majority of the length of the strap, whereas the elastic body 110 is generally only at the end portion of the strap coupled to the cables. This arrangement may be modified so the inelastic body 112 is lengthened and need not form a majority of the length of the strap.

Figure 14:
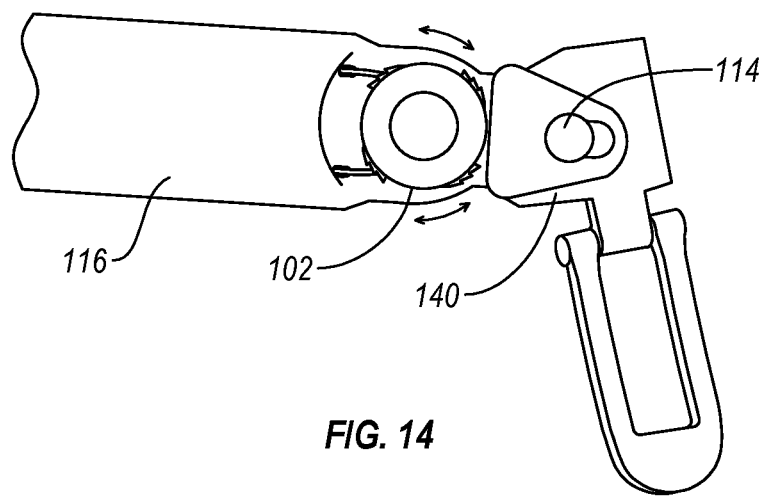
FIG. 14 is a front schematic view of the progressive strap assembly of FIG. 10 pivotally mounted on a buckle.
Figure 15:
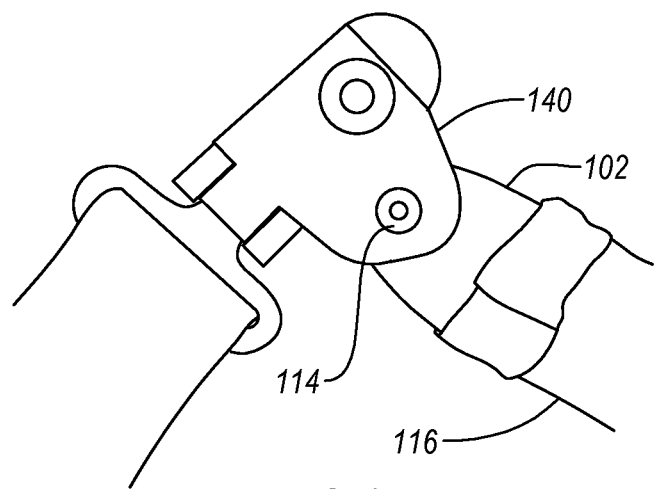
FIG. 15 is a rear schematic view of the progressive strap assembly of FIG. 14.

Unlike in the embodiment of FIG. 4, which forms a button-hole and hook connection to a shell, the pivot point 114 is preferably a rivet that enables the strap assembly 100 to rotate relative to the component upon which it is mounted. In the embodiments of FIGS. 14 and 15, the pivot point 114 is on a buckle 140, which may be secured to a shell, cuff or other component. The pivot point 114 enables the strap assembly to generally conform to the shape of the anatomy individually respective to a user of a brace or support carrying the strap assembly, which attributes to better fit of a brace or support.

The pivot point 114 may be on top or behind a buckle, shell, cuff, or other component depending on the configuration in which the strap assembly is used. This allows flexibility at where the strap assembly 100 can be mounted. By using a pivot point such as a rivet, the strap assembly can be at higher locations on a knee brace, making it easier for a user to reach the tensioning mechanism.

As shown in FIG. 10, the pivot point 114 is preferably located outside of the tensioning mechanism 104. This allows for an area for additional adjustment and does not interfere with the tensioning mechanism 104. In an alternative embodiment, the pivot point may include a ball joint that enables pivoting outward and inward adjustment besides pivoting movement discussed with the rivet pivot point 114.

In this embodiment, the cover 116 is preferably a textile rather than a plastic, rubber, or otherwise formed cover. The textile-based cover can be opened (such as through hook and loop fasteners) so the user or clinician has ready access to adjust or modify the cables. The textile-based cover is also flexible, lower profile and has less bulk.

Figure 11:
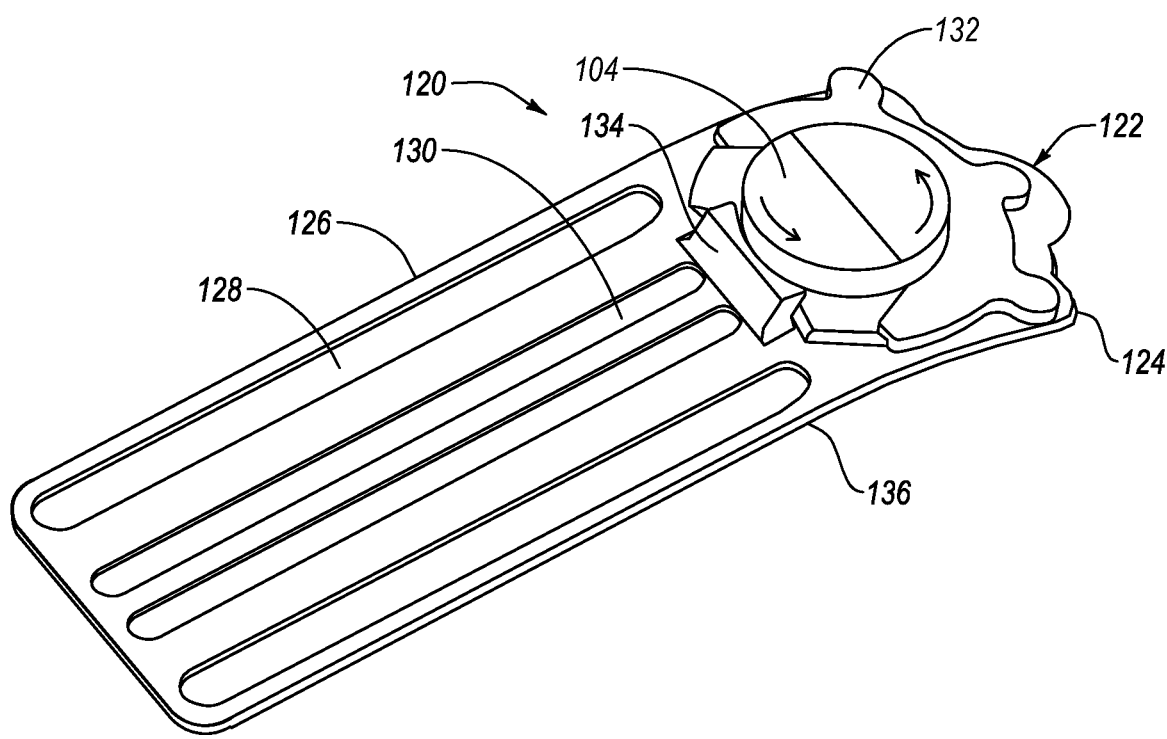
FIG. 11 is a variation of a base plate for a progressive strap assembly.

FIG. 11 depicts a variation of a base plate assembly 120 including a base plate 122 and ratcheting ratcheting device 104. The base plate 122 defines a first portion opposite to a second portion, wherein the first portion of the base plate 122 is located outside the sleeve 116. The base plate 122 further defines a first end 124 having a shorter length than a second end 126. The first and second ends 124, 126 are delimited by a bend 136 enabling the base plate 122 to bend about a user's anatomy.

The first end 124 has a greater thickness than the second end 126, and the thickness may taper between the first and second ends 124, 126. The first end 124 is flexible, although has sufficient rigidity to accommodate the tensioning mechanism 104. Parts 132, 134 are provided to surround at least part of the tensioning mechanism 104 to cover and guard the tensioning mechanism 104.

Figure 12:
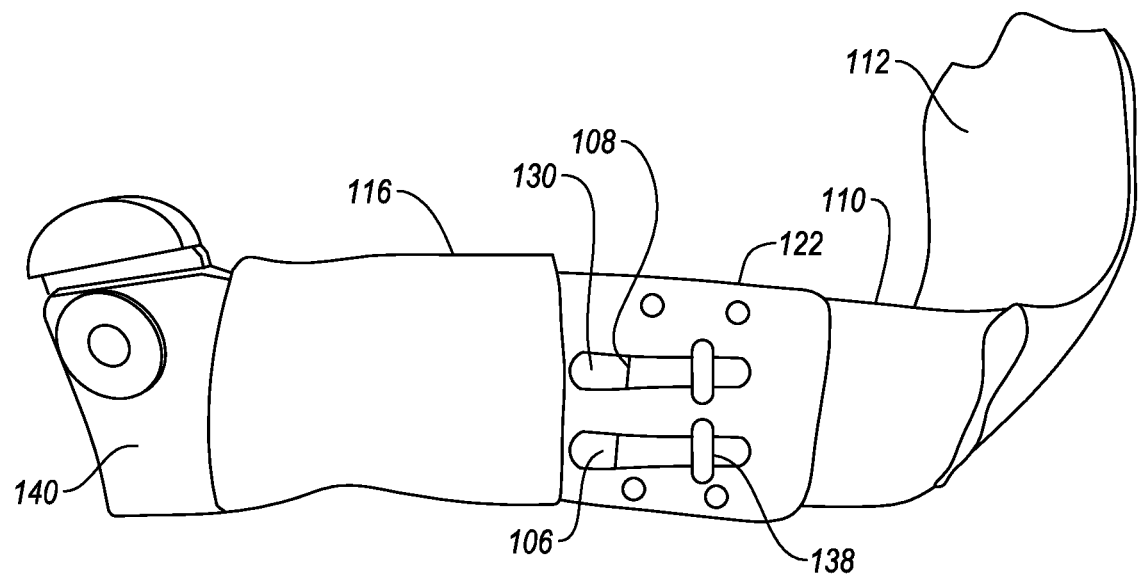
FIG. 12 is a rear schematic view of a progressive strap assembly including the base plate of FIG. 11.
Figure 13:
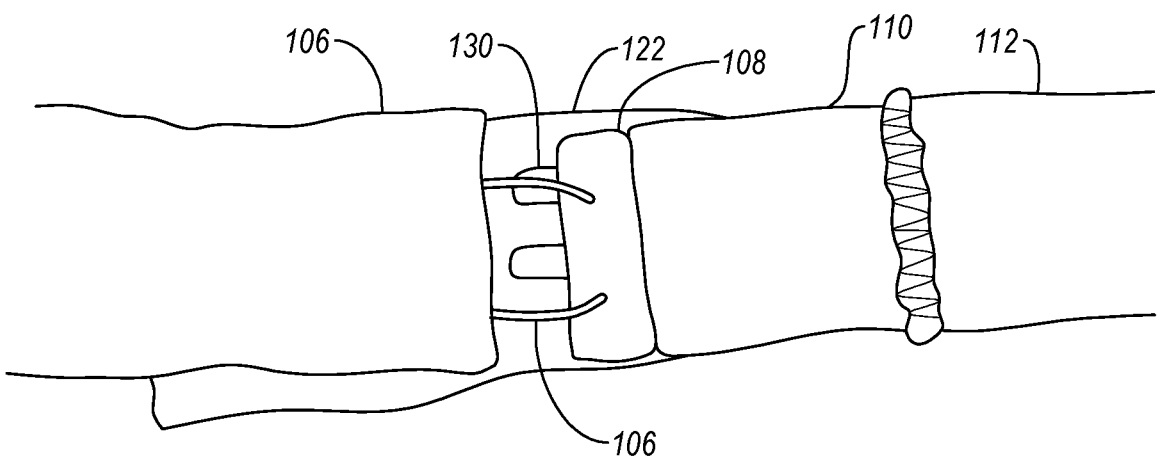
FIG. 13 is a front schematic view of the progressive strap assembly of FIG. 12.

In referring to the variation of FIGS. 12 and 13, the second end defines a plurality of slots 128 arranged to receive sliders 138 on a bottom side of the retainer 108. The sliders 138 permit the retainer 108 and coupled cables 106 to track the motion regardless of the flexure of the base plate 122 over the user's anatomy.

The sliders may be arranged to be removed from the base plate or may have a snap fit connection to the base plate with the base plate having corresponding openings arranged to receive a shaft of the slider. For example, an individual slider has a shaft having a diameter or width less than the width of the outer slot, and a base connected to the shaft having a width greater than a width of the outer slots. The slider is arranged to slide freely on the outside of the base plate and parallel to the base plate. The shaft preferably has a length consistent with the thickness of the base plate.

Returning to FIG. 11, the second end 126 of the base plate 122 defines a plurality of inner slots 130 or tracks that allow for greater flexibility of the second end 126 besides the thinner thickness. This arrangement permits free twisting of the second end 126 of the base plate 122 and allows it to more snugly conform to a user's anatomy, such as a tibia.

Figure 16:
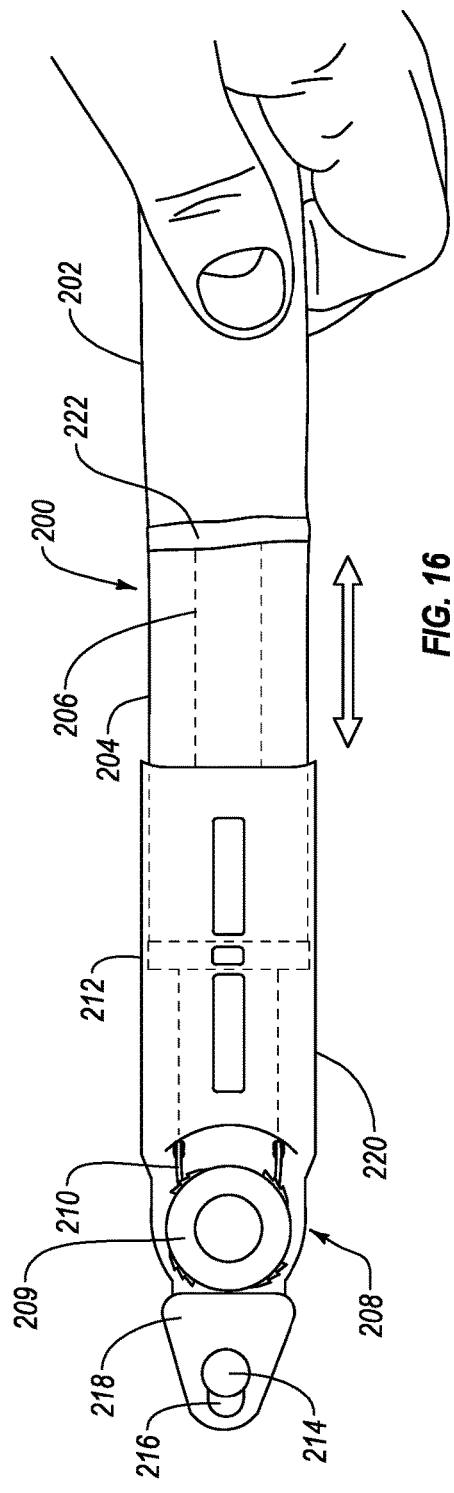
FIG. 16 is a front schematic view of a variation of the progressive strap assembly of FIG. 10.

According to the exemplary embodiment of FIG. 16, a progressive strap assembly 200 having a strap including a generally inelastic strap body 202 and an elastic body 204 having a first end at which the inelastic strap body 202 secures along a connection 222 and a tension limiter 206. The connection 222 may comprises a connector, such as a tab or bracket, stitching, or other means for securing the inelastic strap body 202 to the elastic body 204. The connection may be permanent in that removal of the inelastic strap body 202 from the elastic body 204 may damage one or both of the strap bodies, or the connection may be removable in that the inelastic strap body 202 is easily repeatedly securable and removable from the elastic strap body 204.

As with the embodiments described herein, the term "flexible" is distinguished as being bendable, whereas the term "elastic" is distinguished as returning to an original shape or size after being stretched. The term "inelastic" is the opposite of "elastic" in that it is distinguishable as not being capable of being stretched. From the foregoing, a strap body or tension limiter can be flexible in that it bends or yields to a shape, but it cannot be stretched in its longitudinal, lateral, or orthogonal direction to be lengthened greater than a predetermined dimension such as length, width, or thickness. An elastic strap can be pulled greater than an initial relaxed dimension upon applying a force and upon release of the force revert to the initial, relaxed dimension, preferably without permanent or minimal deformation.

The tension limiter 206 is preferably an inelastic strip of a fabric or plastic strip and has a length greater than the elastic body 204 in a relaxed configuration. The tension limiter 206 may be formed as more flexible and lightweight than the inelastic body 202, yet both are inelastic. The tension limiter 206 may be a textile-based strip sized substantially thinner and narrower than the inelastic strap body since the tension limiter is provided to inhibit stretching of the elastic strap body beyond a predetermined length. The tension limiter 206 according to this embodiment is preferably not intended to bear tension forces of the strap assembly over a limb, although it is not limited in being arranged to do so.

In this embodiment the tension limiter 206 has a width less than a width of the elastic body 204 to minimize interaction of the tension limiter 206 with other brace components upon which the progressive strap assembly may secure or other items that may come into contact with the progressive strap assembly. Alternatively, the tension limiter 206 may have a width substantially the same as the elastic body 206.

In a variation, the tension limiter 206 may comprise a plurality of stitches along its length in a similar manner as in the embodiment of FIG. 6, but formed on a strip of material separate from the elastic body 204. The plurality of stitches may be formed in a variety of non-linear configurations wherein a matrix or substrate carrying the stitches is elastic, and the stitches, when fully elongated from the non-linear configurations, inhibit further stretching of the matrix or substrate. In another variation, the stitches may be in a linear configuration but arrive at a maximum stretched length before the elastic body does, thereby inhibiting further stretching of the elastic body beyond the maximum stretched length of the stitches.

In a variation, the tension limiter is defined by an inelastic segment of the inelastic body overlapping the entire length of the elastic body. The inelastic segment has a length greater than the elastic body when the elastic body is in a relaxed condition and is secured to the first and second ends of the elastic body. The inelastic segment may have the same width as the elastic body or may have a reduced width.

A dosing device 208 including a tensioning mechanism 209 has at least one elongate element 210, such as a cable, securing to a retainer 212, such as a tab, secured to a second end of the elastic strap body 204. A sleeve 220, of any of the types described herein, may cover portions of the at least one elongate element 210, the retainer 212, the inelastic strap body 202 and the tension limiter 206. The tensioning mechanism 209 and sleeve 220 may be carried by a base 218 belonging to the dosing device 208 securable to a brace or frame element (not shown). The base 218 may include a slot or keyhole features 216 engageable with a pin or support 214 connecting to the brace or frame element.

The dosing device may include the features of the foregoing dosing device embodiments, including sliders and retainer, to permit the elastic body to stretch and adjust in a controlled manner.

The progressive strap assembly may be devoid of a dosing device and instead the end of the progressive strap assembly comprises the second ends of the elastic body and tension limiter, with or without the retainer. In a variation, the progressive strap assembly includes first and second inelastic bodies secured to the first and second ends of the elastic body, such that the elastic body is bordered at opposed ends by inelastic bodies, rather than merely being at or defining in part an end portion of the progressive strap assembly.

Figure 17:
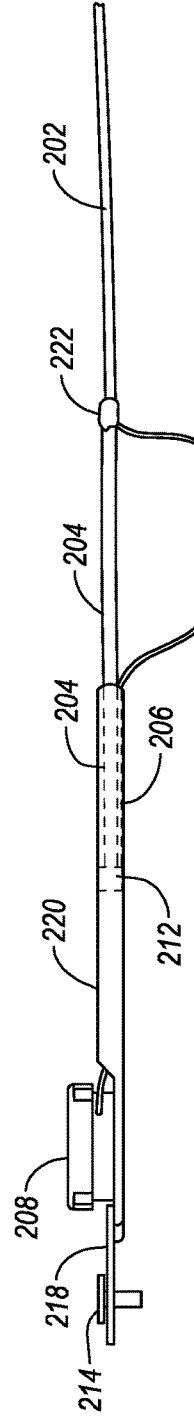
FIG. 17 is a side view of the progressive strap assembly of FIG. 16 in a first, relaxed condition.
Figure 18:
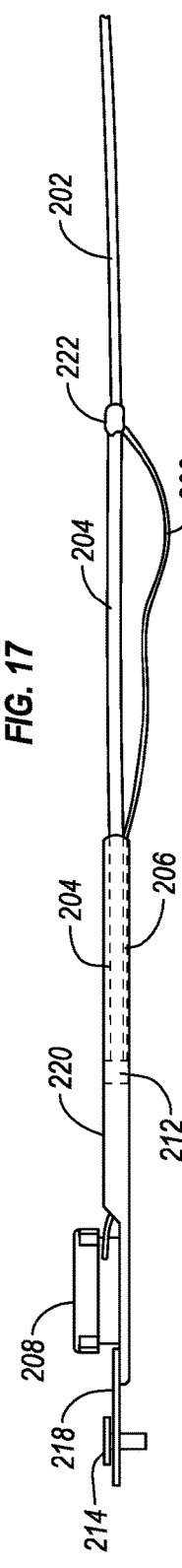
FIG. 18 is a side view of the progressive strap assembly of FIG. 16 in a second, intermediate condition.
Figure 19:
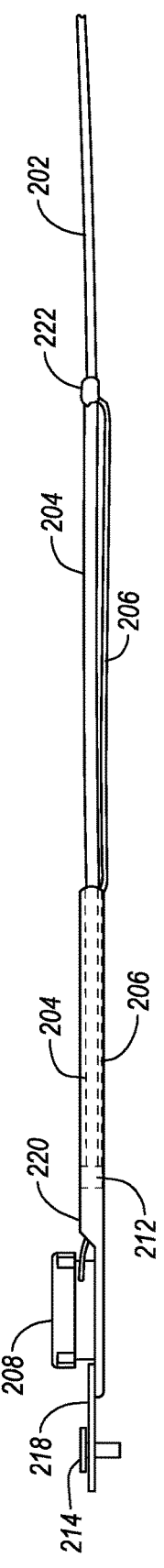
FIG. 19 is a side view of the progressive strap assembly of FIG. 16 in a third, tensioned condition.

Referring to the schematic views of FIGS. 17-19, FIG. 17 shows progressive strap assembly 200 in a relaxed condition, particularly with both the elastic strap body 204 in a non-tensioned state and tension limiter 206 slackened. FIG. 18 exemplifies an intermediate condition wherein the progressive strap assembly 200 undergoes some tensioning with the elastic strap body 204 being pulled toward and by the tensioning mechanism 209 and increasing in length, and the tension limiter 206 being reduced in slack according to the increase in length of the elastic strap body 204. FIG. 19 depicts the progressive strap assembly 200 in a fully tensioned condition by further operation of the tensioning mechanism 209 wherein the length of the elastic strap body 204 is further inhibited by the tension limiter 206 in a taut condition. The length of the elastic strap body 204 is generally the same as the length of the tension limiter 206 in the fully tensioned condition.

Figure 20:
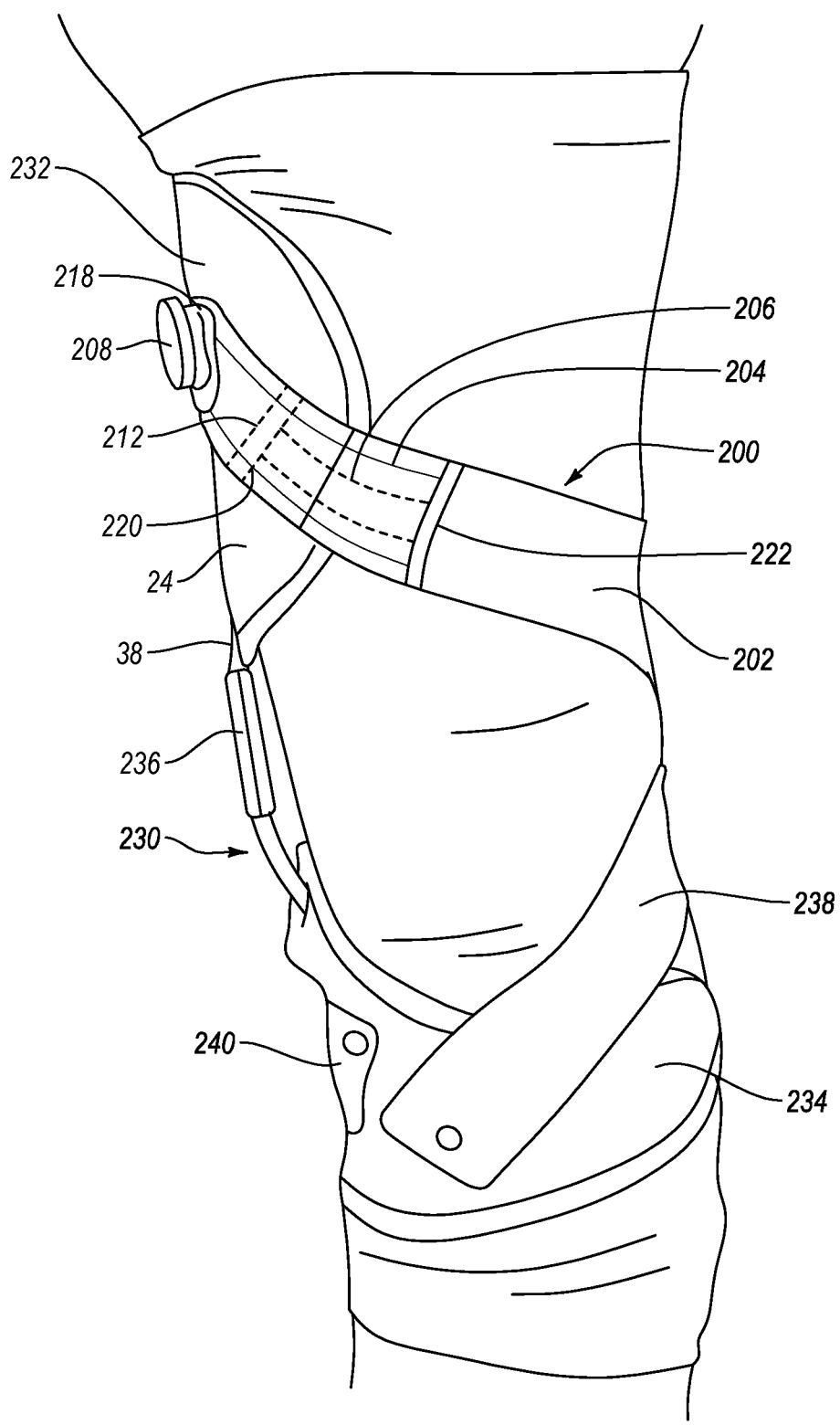
FIG. 20 is an exemplary embodiment of the progressive strap assembly of FIG. 16 on an orthopedic device.

FIG. 20 shows the progressive strap assembly 200 arranged with an orthopedic device 230. The orthopedic device 230 is in an exemplary embodiment of a knee brace. The base 218 connects to an upper frame 232, and the progressive strap assembly 200 spirals toward a lower frame 234 at which a second end 240 of the inelastic strap body 202 secures. The upper and lower frames 232, 234 connect to one another by a hinge assembly 236. An additional strap assembly 238 may be arranged between the upper and lower frames 232, 234 in an opposing orientation to the progressive strap assembly 200.

It should be remembered that the illustrative examples of FIGS. 17-19 are depicted without being on a leg of a user. During use, whether according to different positions of gait such as flexion and extension or due to anatomical changes in a user's leg, the tensioning condition of elastic strap body may vary with or without tensioning resulting from the tensioning mechanism. Rather, the elastic strap body accommodates movement of a knee or other joint while maintaining or approximating force over the leg or other limb.

Various embodiments and methods for using the same may be devoid of a tension limiter used in combination with the elastic body. Rather, the dimension or dimensions of the elastic body such as length, width, and thickness and the elasticity of the elastic body may be selected so the maximum stretchable length is obtainable without a tension limiter and the progressive strap assembly can be operable with only at least one elastic body and at least one inelastic body.

It is to be understood that not necessarily all objects or advantages may be achieved under any particular embodiment of the disclosure. For example, those skilled in the art will recognize that the orthopedic device and progressive strap assembly may be embodied or carried out to achieve or optimize one advantage or group of advantages as taught without achieving other objects or advantages as taught or suggested herein.

The skilled artisan will recognize the interchangeability of various disclosed features. Besides the variations described, other known equivalents for each feature can be mixed and matched by one of ordinary skill in this art to construct an orthopedic device under principles of the present disclosure. It will be understood by the skilled artisan that the features described may be adapted to other types of orthopedic devices. Hence this disclosure and the embodiments and variations are not limited to knee braces, but can be utilized in any orthopedic devices.

Although this disclosure describes certain exemplary embodiments and examples of an orthopedic device, it therefore will be understood by those skilled in the art that the present disclosure extends beyond the disclosed knee brace embodiments to other alternative embodiments and/or uses of the disclosure and obvious modifications and equivalents. It is intended that the scope of the present disclosure should not be limited by the disclosed embodiments described above, and may be extended to orthopedic devices and supports, and other applications that may employ the features described.

The invention claimed is:

1. A progressive strap assembly, comprising:
a strap body having a first length and a first end, the strap body having a first elasticity being substantially inelastic;
an elastic body having a second elasticity greater than the first elasticity, the elastic body defining first and second ends, the first end of the elastic body secured to the first end of the strap body by stitching;
a retainer having a first end secured to the second end of the elastic body, the retainer having a second end opposite to the first end;
a base plate having a first portion opposite to a second portion, wherein the base plate defines a first end having a shorter length than a second end, the first and second ends of the base plate being delimited by a bend arranged to enable the base plate to bend about a user's anatomy;
a tensioning mechanism coupled to the second end of the retainer by at least one elongate element, the tensioning mechanism arranged for incremental adjustment of a length of the at least one elongate element between the tensioning mechanism and the retainer;
wherein the second end of the base plate defines at least one slot arranged to receive a slider extending from the retainer, the slider being arranged to slide freely on a surface of the base plate opposite the retainer and the at least one elongate element, in a direction parallel to the base plate;
a flexible sleeve secured to the base plate through which the second portion of the base plate and the at least one elongate element extend, the second ends of the retainer and the elastic body are arranged to linearly slide within the flexible sleeve.

2. The progressive strap assembly of claim 1, wherein the at least one elongate element forms two segments connecting the tensioning mechanism to the retainer.

3. The progressive strap assembly of claim 2, wherein the tensioning mechanism includes a ratcheting device coupled to the at least one elongate element, the at least one elongate element is a cable.

4. The progressive strap assembly of claim 1, wherein the first portion of the base plate is located outside of the sleeve.

5. The progressive strap assembly of claim 1, wherein the first end of the base plate has a greater thickness than the second end of the base plate.

6. The progressive strap assembly of claim 1, wherein a thickness between the first and second ends of the base plate tapers, wherein the first end of the base plate is flexible.

7. The progressive strap assembly of claim 1, wherein the slider has a shaft with a diameter or width less than a width of the at least one slot, and a base connected to the shaft having a width greater than the width of the at least one slot.

8. The progressive strap assembly of claim 1, wherein the flexible sleeve is formed from a textile.

9. A progressive strap assembly, comprising:
a strap body having a first length and a first end, the strap body having a first elasticity being substantially inelastic;
an elastic body having a second elasticity greater than the first elasticity, the elastic body defining first and second ends, the first end of the elastic body secured to the first end of the strap body by stitching;
a retainer having a first end secured to the second end of the elastic body, the retainer having a second end opposite to the first end;
a base plate having a first portion opposite to a second portion, wherein the base plate defines a first end having a shorter length than a second end, the first and second ends of the base plate being delimited by a bend arranged to enable the base plate to bend about a user's anatomy;
a tensioning mechanism coupled to the second end of the retainer by at least one elongate element, the tensioning mechanism arranged for incremental adjustment of a length of the at least one elongate element between the tensioning mechanism and the retainer, the tensioning mechanism including a ratcheting device;
the at least one elongate element including a cable secured to the retainer and received by the ratcheting device;
wherein the second end of the base plate defines at least one slot arranged to receive a slider extending from the retainer, the slider being arranged to slide freely on a surface of the base plate opposite the retainer and the at least one elongate element, in a direction parallel to the base plate;
a flexible sleeve secured to the base plate through which the second portion of the base plate and the at least one elongate element extend, the second ends of the retainer and the elastic body are arranged to linearly slide within the flexible sleeve.

10. A progressive strap assembly, comprising:
a strap body having a first length and a first end, the strap body having a first elasticity being substantially inelastic;
an elastic body having a second elasticity greater than the first elasticity, the elastic body defining first and second ends, the first end of the elastic body secured to the first end of the strap body, the strap body forming a majority of a length of a strap formed by the strap body and the elastic body;
a retainer having a first end secured to the second end of the elastic body, the retainer having a second end opposite to the first end;
a base plate having a first portion opposite to a second portion, wherein the base plate defines a first end having a shorter length than a second end, the first and second ends of the base plate being delimited by a bend arranged to enable the base plate to bend about a user's anatomy;
a ratcheting device coupled to the second end of the retainer by a cable, the ratcheting device arranged for incremental adjustment of a length of the cable between the ratcheting device and the retainer;
wherein the second end of the base plate defines at least one slot arranged to receive a slider extending from the retainer, the slider being arranged to slide freely on a surface of the base plate opposite the retainer and the cable, in a direction parallel to the base plate;
a flexible sleeve secured to the base plate through which the second portion of the base plate and the cable extend, the second ends of the retainer and the elastic body are arranged to linearly slide within the flexible sleeve, the flexible sleeve being formed by a textile.

* * * * *